United States Patent [19]

Phadke et al.

[11] Patent Number: 5,437,873

[45] Date of Patent: Aug. 1, 1995

[54] SUPERIOR TASTING PHARMACEUTICAL COMPOSITION HAVING POROUS PARTICLES AND THE PROCESS OF PREPARING SUCH PHARMACEUTICAL COMPOSITION

[75] Inventors: Deepak S. Phadke; Melissa P. Neddermeyer, both of Indianapolis, Ind.

[73] Assignee: Merrell Dow Pharmaceuticals Inc., Cincinnati, Ohio

[21] Appl. No.: 184,613

[22] Filed: Jan. 19, 1994

Related U.S. Application Data

[60] Division of Ser. No. 884,299, May 12, 1992, Pat. No. 5,302,396, which is a continuation of Ser. No. 606,284, Oct. 31, 1990, abandoned, which is a continuation-in-part of Ser. No. 586,351, Sep. 21, 1990, abandoned.

[51] Int. Cl.$^6$ .......................... A61K 9/16; A61K 9/20
[52] U.S. Cl. ..................... 424/465; 424/439; 424/452; 424/458; 424/466; 424/470; 424/489; 424/464; 514/819
[58] Field of Search ............... 424/452, 458, 465, 466, 424/470, 489, 464

[56] References Cited

U.S. PATENT DOCUMENTS

| | | | |
|---|---|---|---|
| 2,999,293 | 9/1961 | Taff et al. | 25/156 |
| 3,653,914 | 4/1972 | Schmitt | 99/78 |
| 4,684,534 | 8/1987 | Valentine | 427/3 |
| 4,965,072 | 10/1990 | Alexander et al. | 424/458 |

OTHER PUBLICATIONS

Jachowicz, Renata, *International Journal of Pharmaceutics,* 35, (1987) pp. 7–12.
Jachowicz, Renata, *International Journal of Pharmaceutics,* 35, (1987) pp. 1–5.
Ford, James L., *Pharm. ACTA Helv.,* 61(3), (1986), pp. 69–88.
Stavchansky, Stan et al., *J. Pharm. Sciences,* 73(6), (1984) pp. 733–736.
Sekikaqa, Hitoshi et al., *Chem Pharm. Bull,* 31(4) (1983) pp. 1350–1365.
Kaur, Rabinder et al., *Journal of Pharm. Sciences,* vol. 69, No. 11, Nov. 1980, pp. 1321–1326.
Takayama, Kozo et al., *Chem Pharm. Bull,* 28(1) (1980) pp. 3304–3309.
Chiou et al., *Journal of Pharm. Sciences,* vol. 60, No. 9 (Sep. 1971) pp. 1281–1302.
Goldberg, Arthur H. et al., *Journal of Pharm. Sciences,* vol. 55, No. 5 (1966) pp. 487–492.

*Primary Examiner*—Thurman K. Page
*Assistant Examiner*—James M. Spear
*Attorney, Agent, or Firm*—Michael J. Sayles

[57] ABSTRACT

The present invention is directed towards a process for producing a superior tasting pharmaceutical composition having porous granules produced through in situ gas generation using effervescence-producing ingredients. The method disclosed herein is especially suitable for producing superior tasting antacid tablets as well as superior tasting calcium supplements.

15 Claims, No Drawings

SUPERIOR TASTING PHARMACEUTICAL COMPOSITION HAVING POROUS PARTICLES AND THE PROCESS OF PREPARING SUCH PHARMACEUTICAL COMPOSITION

CROSS REFERENCE TO RELATED APPLICATIONS

This is a division of application Ser. No. 07/884,299, filed May 12, 1992, Patent Allowed Nov. 4, 1993; U.S. Pat. No. 5,302,396 which is a continuation of Ser. No. 07/606,284, filed Oct. 31, 1990, now abandoned; which is a continuation-in-part of 07/586,351, filed Sep. 21, 1990, now abandoned.

BACKGROUND OF THE INVENTION

A superior tasting pharmaceutical composition having porous particles and the novel process for preparing said pharmaceutical composition is disclosed herein. The improved pharmaceutical composition is especially well suited for preparing pharmaceutical compositions of antacids such as aluminum hydroxide and magnesium hydroxide which typically have a chalky and gritty taste and are therefore unpleasant to administer orally. The prior art describes the use of fluid bed granulators that produce porous granules. In this novel approach, effervescence-producing ingredients are used for preparing porous granules.

SUMMARY OF THE INVENTION

The process described in further detail below can be summarized as follows. Stoichiometric amounts of an appropriate base and an appropriate acid are mixed and compressed in a press to form a compact. The compact is then milled to form an evenly distributed stoichiometric mixture of the base and the acid. A pharmacologically active agent is then added to the mixture to form an active mixture that is then granulated in admixture with an appropriate amount of a granulating agent, such appropriate amount being well-known in the art, wherein the granulating agent in combination with the active mixture forms a wet granulation having minimal water activity. The wet granulated material is then dried whereby the applied heat and the water cause the acid and the base to react releasing gas from the wet granulation to form porous particles. The porous particles are then milled to form a powder which can be compressed to form a tablet suitable for oral administration.

It is important to note that the essential feature of the present invention is the production of a pharmaceutical composition of porous particles incorporating the pharmacologically active agent. In this respect, therefore, the exact order of the steps in producing such porous particles is unimportant.

For example, the approximately stoichiometric amounts of an appropriate acid and an appropriate base can be milled separately and then mixed to form the effervescent mixture. The effervescent mixture is then added to a preparation of a pharmacologically active agent to form an active mixture. The active mixture is then granulated in admixture with an appropriate amount of a granulating agent, such appropriate amount being well-known in the art, to form a wet granulation containing water. The wet granulation is then dried with applied heat such that the applied heat and the water in the wet granulation cause the acid and the base to react releasing gas from the wet granulation to form porous particles. The porous particles can then be milled to form a powder, which can be compressed to form a tablet, used in a reconstitutable powder dosage form or filled in a capsule as a quick dissolving powder.

Likewise, the stoichiometric amounts of an appropriate acid and an appropriate base can be mixed to form a mixture of the appropriate acid and the appropriate base. The mixture of the appropriate acid and the appropriate base is then granulated with an appropriate amount of a non-aqueous granulating liquid containing a binding agent dissolved in absolute alcohol to produce a wet granulation. The wet granulation is then dried to form granules of the mixture of the appropriate acid and the appropriate base, which are then milled to form an effervescent mixture of fine particle size. The effervescent mixture of fine particle size is then added to a preparation of a pharmacologically active agent to form an active mixture. The active mixture is then granulated in admixture with an appropriate amount of a granulating agent, such appropriate amount being well-known in the art, to form a wet granulation containing water. The wet granulation is then dried with applied heat such that the applied heat and the water cause the acid and the base to effervesce, forming porous particles. The porous particles can then be milled to form a powder, which can be compressed to form a tablet, used in a reconstitutable powder dosage form or filled in a capsule as a quick dissolving powder.

A preferred embodiment of the invention is where the active ingredient is an antacid such as aluminum hydroxide or magnesium hydroxide or a combination thereof or such combination in combination with other antacids. A more preferred embodiment of the invention is where the acid is citric acid, tartaric acid, malic acid or maleic acid and the base is sodium or potassium bicarbonate or sodium or potassium carbonate. Other preferred embodiments include compositions in which the active agent is a calcium supplement, such as calcium carbonate, or a reconstitutable powder having methylcellulose, hydroxypropylmethylcellulose or other similar agents as the active agent.

DETAILED DESCRIPTION OF THE INVENTION

The present invention is directed towards a process for producing a superior tasting pharmaceutical composition having porous granules produced through in situ gas generation using effervescence-producing ingredients. The process is useful for preparing pharmaceutical compositions having active ingredients that are hydrophobic by nature and that have a chalky and/or gritty taste such as antacids and calcium supplements. The composition may also prove useful in the delivery of pharmacological agents such as terfenadine as well.

The use of high shear mixers in wet granulation can produce hard granules with low porosity. A commercially available process claims to produce antacid tablets with a less gritty taste using porous granulations made in a fluid bed granulator. This novel, yet simple, approach involves the use of effervescence-producing ingredients for preparing pharmaceutical compositions having porous calcium carbonate granules as well as compositions having porous magaldrate granules. It will be appreciated that other formulations including aluminum hydroxide and magnesium hydroxide, as well as various combinations thereof, are also encompassed within the scope of the invention, as well as other pharmaceutically active agents.

Calcium carbonate was granulated in a laboratory high shear mixer using 10% W/W pregelatinized starch as the binder, water or simple syrup as the granulating liquid, and an effervescent mixture of sodium bicarbonate and citric acid for in situ gas generation during the process to increase the granule porosity. Compacts of a stoichiometric mixture of sodium bicarbonate and citric acid were prepared using a hydraulic press. It will be understood that other mixtures of acids and bases could also be used in this process, including sodium carbonate, potassium bicarbonate, potassium carbonate, tartaric acid, malic acid, maleic acid, etc. It will be recognized that this list is not exhaustive and that other acids and bases are encompassed within the scope of the invention as well.

The compacts were ground and used at 1.76% and 3.52% W/W levels in the preparation of calcium carbonate granulations. A calcium carbonate granulation prepared without the effervescent mixture was used as the control. The bulk and tap density, and the mercury intrusion porosimetry data on the individual cuts showed that the granules prepared using this approach have greater porosity than the control granules. The $-40+60$ and $-60+80$ sieve cuts of the porous and control granules were compressed on a hydraulic press. A taste test was conducted which showed that the granules prepared using this approach and the tablets made therefrom were less gritty than the control samples and tended to dissolve in the mouth giving a superior taste and mouth feel.

This novel, yet simple approach was also used to prepare porous mannitol granules. Mannitol granulations were prepared in a laboratory high shear mixer using 10% W/W pregelatinized starch as the binder, water as the granulating liquid, and an effervescent combination of sodium bicarbonate and citric acid for in situ gas generation during the process to increase the granule porosity. A stoichiometric mixture of sodium bicarbonate and citric acid was first compressed on a hydraulic press and the compacts were ground and used at 1.76%, 2.64%, 3.52%, and 4.40% W/W levels in the preparation of mannitol granulations. Several process conditions were tried for maximizing the granule porosity. Control mannitol granulations were also prepared in a fluid bed granulator using the same formula and process but without the effervescent mixture. The bulk and tap densities of the various sieve cuts of these granulations were measured. Similarly, the porosity of the individual sieve cuts was measured using a mercury intrusion porosimeter. The results of this comparison indicate that the porosity of mannitol granules could be increased through in situ gas generation using effervescence-producing ingredients under controlled granulating conditions.

In another approach to testing the efficacy of increasing granule porosity through in situ gas generation using effervescence-producing ingredients, mannitol, sodium bicarbonate, citric acid anhydrous, pregelatinized starch and hydroxypropyl methylcellulose (HPMC) were used. The granulations were prepared in a high shear mixer and dried in an oven at 130° F. In an attempt to increase the granule porosity efforts were made to minimize the amount of the effervescent reaction taking place during the agglomeration process and thus concentrating the majority of the effervescent reaction in the drying step. In order to minimize the effervescent reaction during the agglomeration process, two approaches were tried. The first approach used a dispersion of hydroxypropyl methylcellulose in water or isopropanol instead of the plain deionized water. The second approach used a refrigerated powder blend and cold (10° C.) water as the granulating liquid. To investigate the effect of the effervescent-mixture concentration on granule porosity, granulations containing 1.76%, 2.64%, 3.52% and 4.40% w/w levels of the effervescent mixture were prepared. Control granularions of mannitol without the effervescent mixture were also prepared for comparison. The $+16$, $-16+20$, $-20+40$, $-40+60$, $-60+80$ and $-80$/pan sieve cuts of the dried granulations were separated using a sieve shaker. The bulk and tap density of the individual sieve cuts was also measured. Similarly, the porosity of the individual sieve cuts was also measured using mercury porosimeter and the porosity (% v/v) was calculated from the mercury intrusion volume and the true density data.

SUMMARY OF RESULTS

The bulk and tap density values for the various sieve cuts of the control and porous (1.76% w/w effervescent mixture) granules are tabulated below.

| Sieve Cut | Bulk Density (g/cc) | | Tap Density (g/cc) | |
|---|---|---|---|---|
| | Control | Porous | Control | Porous |
| $-16 + 20$ | 0.44 | 0.42 | 0.46 | 0.45 |
| $-20 + 40$ | 0.48 | 0.45 | 0.50 | 0.48 |
| $-40 + 60$ | 0.53 | 0.49 | 0.55 | 0.53 |
| $-60 + 80$ | 0.54 | 0.52 | 0.59 | 0.57 |

The above bulk and tap density data indicate that for each sieve cut the porous granules had lower density values than the control samples. This trend was also observed for the batches made using different levels of the effervescent mixture.

The total mercury intrusion volume and the percent porosity for the $+16$, $-16+20$, and $-40+60$ sieve cuts of the control and porous (1.76% w/w effervescent mixture) granules are tabulated below.

| Sieve Cut | Intrusion Volume (cc/g) | | Percent Porosity (% v/v) | |
|---|---|---|---|---|
| | Control | Porous | Control | Porous |
| $+16$ | 0.27 | 0.39 | 28.4 | 36.1 |
| $-16 + 20$ | 0.26 | 0.36 | 27.7 | 34.3 |
| $-40 + 60$ | 0.21 | 0.25 | 23.6 | 26.6 |

The percent porosity values for all three sieve cuts of the porous granules were higher than the control granules.

The total mercury intrusion volume and the percent porosity for the $-40+60$ sieve cut of the control and porous granules prepared using dispersions of HPMC in deionized water and isopropanol as the granulating liquid are shown below.

| | Intrusion Volume (cc/g) | | Percent Porosity (% v/v) | |
|---|---|---|---|---|
| | Control | Porous | Control | Porous |
| HPMC/Water | 0.27 | 0.33 | 28.4 | 32.4 |
| HPMC/Isopropanol | 0.39 | 0.40 | 35.2 | 36.7 |

The above results indicate that the granule porosity increased when the HPMC dispersion in water was used as the granulating liquid. Although the granule porosity was higher for both the control and porous granules for the granulations prepared using the HPMC dispersion in isopropanol, there was no marked difference between the control and the porous granules. This would be expected since water is needed for the effervescent reaction.

The mercury intrusion volume and the percent porosity for the −40+60 sieve cut of the control and porous granules prepared using room temperature and refrigerated powder blends are shown below.

|  | Intrusion Volume (cc/g) | | Percent Porosity (% v/v) | |
| --- | --- | --- | --- | --- |
|  | Control | Porous | Control | Porous |
| Room temperature | 0.21 | 0.26 | 23.6 | 27.4 |
| Refrigerated | 0.21 | 0.25 | 23.6 | 26.6 |

The above results indicate that refrigerating the powder blend prior to granulation did not increase the granule porosity to any greater extent than the granules prepared using the room temperature powder blend.

The following examples are illustrative of the method of preparing superior tasting, pharmaceutical compositions having porous particles according to the disclosed invention and are not to be construed as limiting in any way.

EXAMPLE 1

STEP 1

First, 11.4 g sodium bicarbonate and 8.6 g citric acid, anhydrous, are combined and then compressed into 1 g compacts using a Carver press applying 10,000 pounds of force. The compacts are stored in a desiccator overnight. The compacts are then milled by the following procedure:
(a) milling the compacts for 10 seconds;
(b) allowing the mill to cool for 10 seconds; and
(c) milling for another 10 seconds.

The milled powder is then stored in a desiccator overnight.

STEP 2

Calcium carbonate (671.6 g) and pregelatinized starch (75.0 g) are passed through a 20 mesh screen and then placed in a small Lodige mixer. The milled sodium bicarbonate/citric acid powder (3.4 g) is then added to the high shear mixer and the mixture is mixed for 2 minutes. Simple syrup (120 ml) is added while mixing and the mixing is continued for a period of one minute and thirty seconds. The mixer sides are scraped and the mixture is mixed for an additional 30 seconds. The wet granulation is then passed through a 10 mesh screen. The granulation is tray dried in an oven at 130° F. for six hours and then compressed into 558 mg tablets on a hydraulic press.

EXAMPLE 2

Magaldrate (667.5 g) and Starch 1500 (75.0 g) are passed through a 20 mesh screen and added to a small high shear mixer. Milled sodium bicarbonate/citric acid powder (7.5 g), prepared as above in Example 1, Step 1, is added to the mixer. The magaldrate, Starch 1500, and sodium bicarbonate/citric acid milled powder is mixed for 2 minutes and 360 ml of simple syrup is added while mixing for 4 minutes and 15 seconds. The wet granulation is passed through a 10 mesh screen. The granulation is tray dried in an oven at 130° F. for six hours and then dried for another 4 hours at 170° F. The granulation is then milled using a comil, lubricated and flavored and then compressed into 2 g tablets on a hydraulic press.

What is claimed is:

1. A method of preparing a pharmaceutical composition of porous particles comprising:
   (a) mixing stoichiometric amounts of a base selected from the group consisting of sodium bicarbonate, potassium bicarbonate, sodium carbonate and potassium carbonate and an acid selected from the group consisting of citric acid, tartaric acid, malic acid and maleic acid in a press to produce a compact;
   (b) milling the compact to form an evenly distributed effervescent mixture of the acid and the base;
   (c) adding the effervescent mixture to a preparation of a pharmacologically active agent selected from the group consisting of an antacid and a calcium supplement to form an active mixture;
   (d) granulating the active mixture in admixture with an appropriate amount of a granulating agent sufficient to form a wet granulation containing water;
   (e) drying said wet granulation with applied heat whereby the applied heat and the water in the wet granulation cause substantially all of both the acid and the base to react thus releasing gas from the wet granulation to form porous particles;
   (f) milling said porous particles to form a fine powder, which can be compressed to form a tablet, used in a reconstitutable powder dosage form or filled in a capsule as a quick dissolving powder.

2. A method of preparing a pharmaceutical composition of porous particles comprising:
   (a) separately milling stoichiometric amounts of an acid and a base to form a milled acid and a milled base;
   (b) mixing the milled acid and the milled base to form an effervescent mixture;
   (c) adding the effervescent mixture to a preparation of a pharmacologically active agent selected from the group consisting of an antacid and a calcium supplement to form an active mixture;
   (d) granulating the active mixture in admixture with an appropriate amount of a granulating agent sufficient to form a wet granulation containing water;
   (e) drying said wet granulation with applied heat whereby the applied heat and the water in the wet granulation cause substantially both the acid and the base to react thus releasing gas from the wet granulation to form porous particles;
   (f) milling said porous particles to form a fine powder, which can be compressed to form a tablet, used in a reconstitutable powder dosage form or filled in a capsule as a quick dissolving powder.

3. A method of preparing a pharmaceutical composition of porous particles comprising:
   (a) mixing stoichiometric amounts of an acid selected from the group consisting of citric acid, tartaric acid, malic acid and maleic acid and a base selected from the group consisting of sodium bicarbonate, potassium bicarbonate, sodium carbonate and potassium carbonate to form a mixture of the acid and the base;

(b) granulating the mixture of the acid and the base with an amount of a non-aqueous granulating liquid containing a binding agent dissolved in absolute alcohol sufficient to produce a wet granulation;

(c) drying the wet granulation to form granules of the mixture of the appropriate acid and the appropriate base;

(d) milling the granules of the mixture of the acid and the base to form an effervescent mixture of fine particle size;

(e) adding the effervescent mixture of fine particle size to a preparation of a pharmacologically active agent selected from the group consisting of an antacid or a calcium supplement to form an active mixture;

(f) granulating the active mixture in admixture with an amount of a granulating agent sufficient to form a wet granulation containing water;

(g) drying said wet granulation with applied heat whereby the applied heat and the water cause substantially all of both the acid and the base to react releasing gas from the wet granulation to form porous particles;

(h) milling said porous particles to form a fine powder, which can be compressed to form a tablet, used in a reconstitutable powder dosage form, or filled in a capsule as a quick dissolving powder.

4. A pharmaceutical composition of porous particles produced according to the method of claim 1.

5. A pharmaceutical composition of porous particles produced according to the method of claim 2.

6. A pharmaceutical composition of porous particles produced according to the method of claim 3.

7. A pharmaceutical composition of porous particles according to claim 4 wherein the pharmacologically active agent is an antacid.

8. A pharmaceutical composition of porous particles according to claim 5 wherein the pharmacologically active agent is an antacid.

9. A pharmaceutical composition of porous particles according to claim 6, wherein the pharmacologically active agent is an antacid.

10. A pharmaceutical composition of porous particles according to claim 7 wherein the antacid is selected from the group consisting of aluminum hydroxide, magnesium hydroxide or a combination thereof.

11. A pharmaceutical composition of porous particles according to claim 8 wherein the antacid is selected from the group consisting of aluminum hydroxide, magnesium hydroxide or a combination thereof.

12. A pharmaceutical composition of porous particles according to claim 9 wherein the antacid is selected from the group consisting of aluminum hydroxide, magnesium hydroxide or a combination thereof.

13. A pharmaceutical composition of porous particles according to claim 4 wherein the pharmaceutically active agent is calcium carbonate.

14. A pharmaceutical composition of porous particles according to claim 5 wherein the pharmaceutically active agent is calcium carbonate.

15. A pharmaceutical composition of porous particles according to claim 6 wherein the pharmaceutically active agent is calcium carbonate.

* * * * *